(12) United States Patent
Moon et al.

(10) Patent No.: US 10,682,486 B1
(45) Date of Patent: Jun. 16, 2020

(54) SINGLE TREATMENT DISPOSABLE NITRIC OXIDE DELIVERY

(71) Applicants: William Moon, Provo, UT (US); Thomas A. Tait, Box Elder, SD (US)

(72) Inventors: William Moon, Provo, UT (US); Thomas A. Tait, Box Elder, SD (US)

(73) Assignee: Nu-Med Plus Inc., Salt Lake City, UT (US)

(*) Notice: Subject to any disclaimer, the term of this patent is extended or adjusted under 35 U.S.C. 154(b) by 0 days.

(21) Appl. No.: 16/264,642

(22) Filed: Jan. 31, 2019

(51) Int. Cl.
*A61M 16/12* (2006.01)
*A61M 16/00* (2006.01)

(52) U.S. Cl.
CPC ..... *A61M 16/125* (2014.02); *A61M 2016/003* (2013.01); *A61M 2016/0027* (2013.01); *A61M 2202/0275* (2013.01)

(58) Field of Classification Search
CPC ........ A61M 16/125; A61M 2016/0027; A61M 2016/003; A61M 2202/0275
See application file for complete search history.

(56) References Cited

U.S. PATENT DOCUMENTS

| | | | | |
|---|---|---|---|---|
| 4,114,608 A | * | 9/1978 | Russo | A61B 5/0875 128/200.24 |
| 5,058,440 A | * | 10/1991 | Graze, Jr. | G01N 1/2252 73/863.83 |
| 6,089,229 A | * | 7/2000 | Bathe | A61M 16/12 128/203.12 |
| 6,279,574 B1 | * | 8/2001 | Richardson | A61M 16/0096 128/204.18 |
| 2005/0056338 A1 | * | 3/2005 | Hertzler | A61M 15/00 128/200.21 |
| 2006/0060199 A1 | * | 3/2006 | Lampotang | A61M 16/0078 128/205.13 |
| 2007/0144515 A1 | * | 6/2007 | Stenzler | A61M 16/024 128/203.25 |
| 2012/0093948 A1 | * | 4/2012 | Fine | A61M 16/10 424/718 |
| 2014/0352690 A1 | * | 12/2014 | Kolb | A61M 15/0085 128/200.16 |
| 2015/0290417 A1 | * | 10/2015 | Stenzler | A61M 16/085 424/718 |
| 2016/0121071 A1 | * | 5/2016 | Moon | A61M 16/122 128/200.14 |

* cited by examiner

*Primary Examiner* — Timothy A Stanis
*Assistant Examiner* — Jonathan S Paciorek
(74) *Attorney, Agent, or Firm* — Patent Law Office, PC.; Bao Tran

(57) ABSTRACT

A therapeutic level medical gas delivery system includes a pressure regulator with a control point for a flow of medical gas through a critical flow orifice; a variable flow restrictor; and a mixing chamber for the combination of fixed flows.

20 Claims, 2 Drawing Sheets

SINGLE TREATMENT DISPOSABLE NITRIC OXIDE DELIVERY

FIELD OF THE INVENTION

The invention generally relates to the portable storage and dispensing of therapeutic levels of nitric oxide for inhalation by patients.

DESCRIPTION OF RELATED ART

The administration of inhaled nitric oxide (NO) to patients is currently being investigated for its therapeutic effect. The use of NO has a vasodilatory effect on such patients and is particularly of importance in the case of newborns having persistent pulmonary hypertension. In such cases, the administration of NO has significantly increased the oxygen saturation in such infants.

The actual administration of NO is generally carried out by its introduction into the patient as a gas along with other normal inhalation gases given to breathing the patient. Such commercially available supplies are provided in cylinders under pressure and may be at pressures of about 2000 psi and consist of a mixture of NO in nitrogen with a concentration of NO of between about 800-2000 ppm. As such, therefore, some means must be used to reduce the pressure of the supply to acceptable levels for a patient and also to very precisely meter the amount of the NO and nitrogen mixture so that the desired concentration of NO is actually administered to the patient. Such administration must also be added in sympathy with the respiration pattern of the patient.

The concentration administered to a patient will vary according to the patient and the need for the therapy but will generally include concentrations at or lower than 150 ppm. There is, of course, a need for that concentration to be precisely metered to the patient since an excess of NO can be harmful to the patient. In addition, the administration must be efficient in a timely manner in that NO is oxidized in the presence of oxygen to nitrogen dioxide and which is a toxic compound. Therefore, care in its administration is paramount.

Currently known methods of such administration, therefore have been limited somewhat to clinical situations where attending personnel are qualified from a technical sense to control the mixing and administration of the NO to a patient. Such methods have included the use of a forced ventilation device, such as a mechanical ventilator where a varying flow of breathing gas is delivered to the patient as well as gas blenders or proportions that supply a continuous flow of the breathing gas to the patient to which NO has been added.

In the former case, the use of a ventilator is constrained in that the user must know the precise flow from the ventilator and then the amount of NO to be added is determined on a case-to-case and moment-to-moment basis. Furthermore, the flow profile in forced ventilation varies continuously thereby making it impossible to track the flow manually. In the use of the latter gas blenders, the introduction of the NO-containing nitrogen has been accomplished through the use of hand adjustment of a gas proportioner in accordance with a monitor that reads the concentration of NO being administered to the patient. Thus the actual concentration is continuously being adjusted by the user in accordance with the ongoing conditions of the apparatus providing the breathing mixture.

While such modes of providing a known concentration of NO to the patient may be acceptable from a closely controlled and monitored clinical setting, it is advantageous to have a system that could be used without trained technical support and one that is portable for home or emergency use.

U.S. Pat. No. 5,558,083 discloses a nitric oxide delivery system that is useable with any of a variety of gas delivery systems that provide breathing gas to a patient. The system detects the flow of gas delivered from the gas delivery system at various times and calculates the flow of a stream of nitric oxide in a diluent gas from a gas control valve. The flow of gas from the gas delivery system and the flow established from the flow control valve create a mixture having the desired concentration of nitric oxide for the patient.

The system does not have to interrogate the particular gas delivery system being used but is an independent system that can be used with various flows, flow profiles and the like from gas delivery systems.

Another method of dilution consists of pre-diluting the nitric oxide with nitrogen and filling a pressurized steel tank. The drawbacks of this method are the tanks are necessarily large to provide enough gas to complete the treatment, there are multiple dilution steps necessary to create the correct dilution with more chance for errors.

The method that is described here is a dilution method using physical constants to control the process. This type of dilution avoids potential errors. It also allows the delivery system to use a more concentrated gas thereby reducing the size of the equipment and creating a portable device.

SUMMARY

In one aspect, a therapeutic level medical gas delivery system includes a pressure regulator with a control point for a flow of medical gas through a critical flow orifice; a variable flow restrictor; and a mixing chamber for the combination of fixed air flows.

Implementations of the above aspect can include one or more of the following. A vessel can initially be loaded with the medical gas at a pressure greater than atmospheric. A vessel size and a vessel pressure control a quantity of medical gas available for patient treatment. The pressure is dependent on a stability of the gas under pressure. The vessel is coupled to a pressure regulator that controls an outlet pressure of the medical gas. The pressure regulator is a diaphragm, wherein the diaphragm and materials that contact the medical gas are of a material without chemical, catalytic or absorptive interaction. The pressure regulator is set to a pressure that maintains a flow rate of the gas through the critical flow orifice at a desired therapeutic level. The critical flow orifice provides a critical flow of nitric oxide gas when the gas reaches sonic condition. An orifice gas flow comprises an absolute pressure ratio of about 0.5, 0.52, 0.528, or 0.53. An orifice downstream absolute pressure ($P2$) can be approximately 52.8 per cent of an upstream absolute pressure ($P1$). A gas velocity of the gas through the orifice remains constant as the ratio becomes smaller while a mass flow rate increases. An orifice pressure into the orifice at a fixed value is maintained to create a constant mass flow of a nitric oxide gas. The mixing chamber dilutes a fixed mass flow rate to a specified therapeutic level using patient inhalations.

In another aspect, a portable system includes a small pressurized tank is the source of nitric oxide. The tank valve is turned on and the nitric oxide flows through an engineered pathway that delivers a precise amount of nitric oxide gas during each inhalation. The patient uses a face mask connected to the device to inhale the gas. A visual gauge shows the patient the correct rate of inhalation.

In a further aspect, a method of delivering medical gases at therapeutic levels to patients includes providing a vessel that contains nitric oxide at a specified pressure; controlling the pressure for controlled mass flow through a critical flow orifice; controlling the air dilution flow via patient inhalation controlled by a variable restrictor; and maintaining concentration of medical gas through mixing of two fixed mass flows.

Implementations of the above aspect can include one or more of the following. A vessel can initially be loaded with the medical gas at a pressure greater than atmospheric. A vessel size and a vessel pressure control a quantity of medical gas available for patient treatment. The pressure is dependent on a stability of the gas under pressure. The vessel is coupled to a pressure regulator that controls an outlet pressure of the medical gas. The pressure regulator is a diaphragm, wherein the diaphragm and materials that contact the medical gas are of a material without chemical, catalytic or absorptive interaction. The pressure regulator is set to a pressure that maintains a flow rate of the gas through the critical flow orifice at a desired therapeutic level. The critical flow orifice provides a critical flow of nitric oxide gas when the gas reaches sonic condition. An orifice gas flow comprises an absolute pressure ratio of about 0.5, 0.52, 0.528, or 0.53. An orifice downstream absolute pressure (P2) can be approximately 52.8 per cent of an upstream absolute pressure (P1). A gas velocity of the gas through the orifice remains constant as the ratio becomes smaller while a mass flow rate is increased. An orifice pressure into the orifice at a fixed value is maintained to create a constant mass flow of a nitric oxide gas. The mixing chamber dilutes a fixed mass flow rate to a specified therapeutic level using patient inhalations. The pressure regulator is set to a pressure that maintains a flow rate of the gas through the critical flow orifice at a desired therapeutic level. And wherein the critical flow orifice provides a critical flow of nitric oxide gas when the gas reaches sonic condition.

Advantages may include one or more of the following. The system is a small handheld device designed to provide a specified dose of nitric oxide to a patient with each inhaled breath. There are no electronics or batteries. It is powered by the patient's own inhalations. The device is small, portable and is easily disposed of after use. It is ideal for single patient treatment in emergency situations, rapid field deployment and indications requiring short term treatment.

These and other features and advantages of the present invention will be more apparent from the detailed description of the preferred embodiment set forth below, taken in conjunction with the accompanying drawings.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the specification as a whole including the appended claims. It will be understood that dimensions and relative dimensions described and illustrated herein are intended to be by way of example only of specific embodiments and unless otherwise indicated are not intended to limit the scope of the invention. References herein within both the description and claims to specific directions and positions such as "horizontal", "vertical", "forward" and the like are intended only to provide a convenient means of description and are intended to be in reference to the mask in an upright forward-facing position, as if it were worn by a patient in a standing position. Naturally the mask may be used in any orientation.

DETAILED DESCRIPTION

Figure 1:
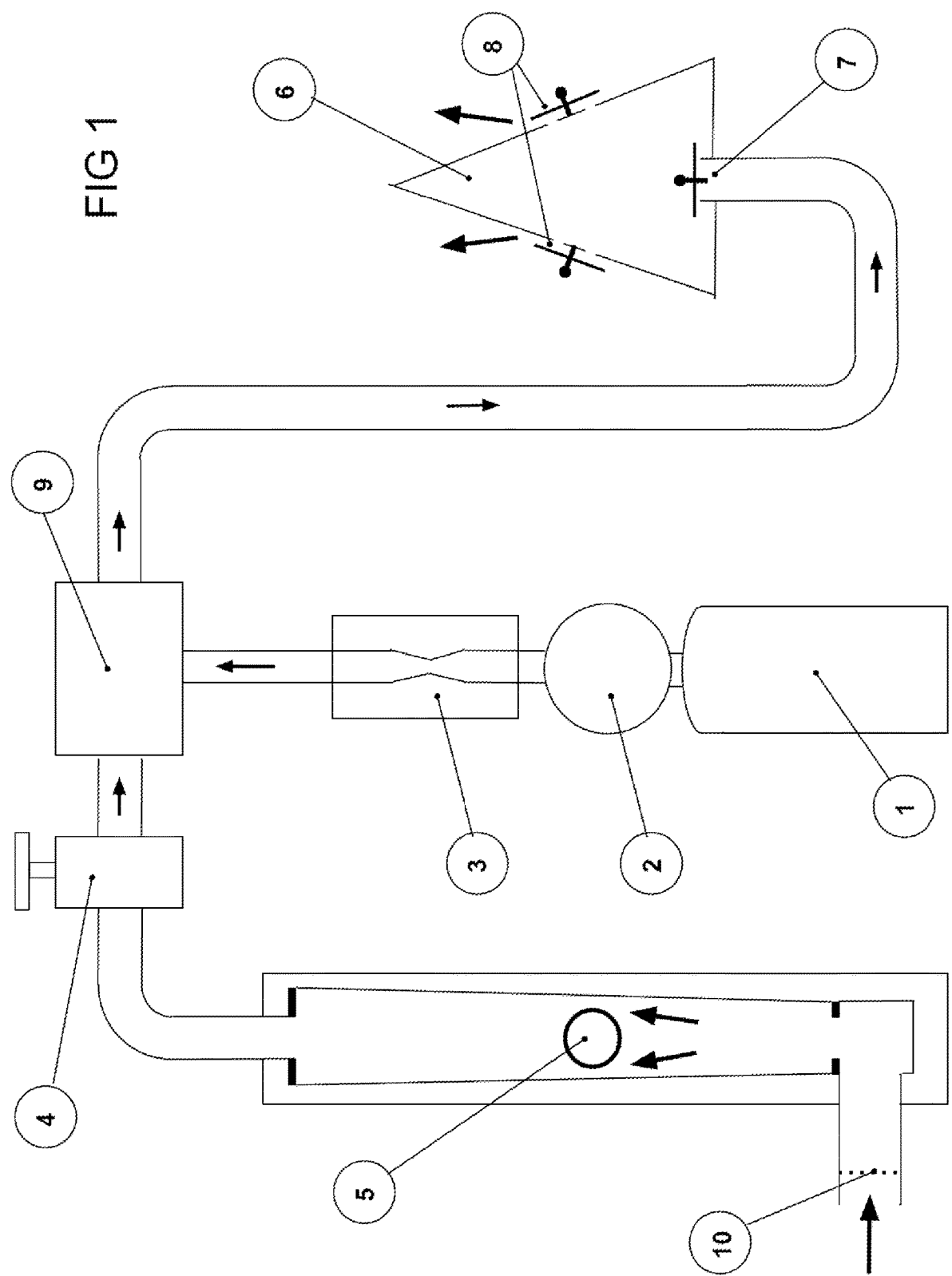
FIG. 1 shows an exemplary schematic diagram of an exemplary single treatment disposable Nitric Oxide delivery system.
Figure 2:
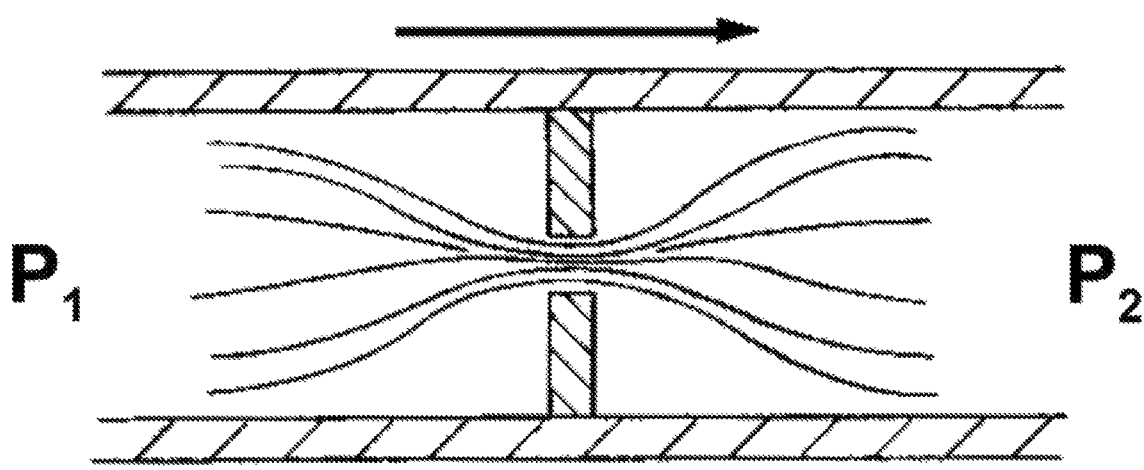
FIG. 2 shows an exemplary gas flow visualization.

As shown in FIG. 1, an exemplary schematic diagram of an exemplary single treatment disposable Nitric Oxide delivery system is shown. The delivery system includes a vessel (1) able to withstand pressure and is inert to nitric oxide. The vessel (1) is filled with a specified concentration of nitric oxide up to and including pure nitric oxide with the diluent at concentrations less than pure being gaseous nitrogen. Pressure is maintained above atmospheric during the filling process.

The vessel is attached directly to a pressure regulator (2) that controls the outlet pressure of the medical gas. The pressure regulator is of the diaphragm type. The diaphragm and other materials that come in contact with the medical gas are of a material that no chemical, catalytic or absorptive interaction takes place between the material and the medical gas. The pressure range is set to a specified pressure before entering a critical flow orifice (3) that regulates the amount of nitric oxide gas flowing out of the orifice. The property of the critical flow orifice is such that the critical flow of the nitric oxide gas occurs when the flowing gas reaches sonic conditions. This occurs for the gas flow when the absolute pressure ratio is 0.528, i.e. when the downstream absolute pressure (P2) is 52.8% of the upstream absolute pressure (P1), FIG. 1. A velocity of the gas through the orifice remains constant as the ratio becomes smaller however the mass flow rate still increases. Maintaining the pressure into the orifice at a fixed value that maintains a P2/P1 ratio of less than 0.528 creates a constant mass flow of the nitric oxide gas. The fixed mass flow rate can now be diluted to a specified therapeutic level using the inhalations of a patient.

Using variable flow restrictor (4) the mass flow of air using the inhalation of the patient can be precisely regulated. The patient can use a visual aid provided by the inline flow indicator (5) maintains a sufficient vacuum to maintain a specified flow of air per inhalation. This flow is measured in liters/min. To aid in achieving the inhalation and the stability of the flow a tightly fitted face mask (6) or mouthpiece is used. A check valve (7) is placed between the face mask/mouthpiece to keep exhalations from entering the dilution/delivery circuit of the device. Exhaled air is exhausted through another check valve (8).

The flow from the nitric oxide supply tank and the air flow from the patient are combined in a mixing chamber (9). The resulting combined flows dilute the nitric oxide gas to the final therapeutic delivery level. A screen (10) is placed over the inlet of the device to keep debris from entering the device and minimizing air current affecting the flow of the nitric oxide into the device. The patient inhales until the flow rate can no longer be maintained and then exhales, readying the device for further inhalations.

The therapeutic concentration can be varied by several control points in the device, the initial concentration of the nitric oxide, the size of the critical flow orifice and the air flow rate created by inhalation. Utilizing these control points results in an extensive range of possible therapeutic concentrations that address a wide range of conditions.

In some configurations, the interface may include a pressure sensor to display pressure to a user. This may be useful in case of constant delivered flow (e.g., high flow) which will cause increased pressure as a flow is left running into a sealed airway.

The various embodiments disclosed herein may be provided in combination with any one or other of the other embodiments or configurations as disclosed here.

The foregoing description of the invention includes preferred forms thereof. Modifications may be made thereto without departing from the scope of the invention.

Numerous further variations and combinations of the features discussed above can be utilized without departing from the spirit of the invention as defined by the claims. Accordingly, the foregoing description of the preferred embodiment should be taken by way of illustration rather than by way of limitation of the invention as claimed.

What is claimed is:

1. A non-electrical therapeutic level medical gas delivery system for a patient, comprising:
   a mechanically controlled pressure regulator configured to have a flow of medical gas through a fixed-diameter-mechanical flow orifice;
   a mechanically-variable flow restrictor; and
   a mechanical mixing chamber for the combination of fixed air flows; and
   a face mask adapted to be sealed over a mouth and a nose, the face mask configured to allow one or more lungs to create a suction force on an inhalation tube to pull the gas and an external air towards the one or more lungs.

2. A system according to claim 1, comprising a vessel loaded with the medical gas at a pressure greater than atmospheric, wherein a vessel size and a vessel pressure control a quantity of medical gas available for patient treatment.

3. A system according to claim 2, wherein the pressure is dependent on a stability of the gas under pressure.

4. A system according to claim 2, wherein the vessel is coupled to the pressure regulator that controls an outlet pressure of the medical gas.

5. A system according to claim 4, wherein the pressure regulator is a diaphragm, wherein the diaphragm that contact the medical gas is without chemical, catalytic or absorptive interaction.

6. A system according to claim 4, wherein the pressure regulator is configured to set a pressure that maintains a flow rate of the gas through the flow orifice at a desired therapeutic level.

7. A system according to claim 1, wherein the flow orifice is configured to provide a predetermined flow of nitric oxide gas when the gas reaches sonic condition.

8. A system according to claim 1, wherein the flow orifice is configured to provide an orifice gas flow with an absolute pressure ratio of about 0.5, 0.52, 0.528, or 0.53.

9. A system according to claim 1, wherein the flow orifice is configured to provide an orifice downstream absolute pressure (P2) of approximately 52.8 per cent of an upstream absolute pressure (P1).

10. A system according to claim 1, wherein the system is configured to have a gas velocity of the gas through the flow orifice constant while a mass flow rate is increased.

11. A system according to claim 1, wherein the system is configured to maintain an orifice pressure into the flow orifice at a fixed value to create a constant mass flow of a nitric oxide gas.

12. A system according to claim 1, wherein the mixing chamber dilutes a fixed mass flow rate to a specified therapeutic level using patient inhalations.

13. A method of non-electrical delivery of medical gases at therapeutic levels to patients comprising:
    providing a vessel that contains nitric oxide at a specified pressure;
    mechanically controlling the pressure for controlled mass flow through a fixed-diameter-mechanical flow orifice;
    controlling air dilution flow via patient inhalation controlled by a mechanically variable restrictor with a fixed mass flow rate; and
    maintaining concentration of medical gas through mixing of two fixed mass flows.

14. A method according to claim 13, wherein the vessel is initially loaded with gas at a pressure greater than atmospheric.

15. A method according to claim 14, wherein a vessel size and a vessel pressure control a quantity of medical gas available for patient treatment.

16. A method according to claim 14, wherein the pressure is dependent on a stability of the gas under pressure.

17. A method according to claim 14, wherein the vessel is coupled to a pressure regulator that controls an outlet pressure of the medical gas.

18. A method according to claim 17, wherein the pressure regulator is a diaphragm, wherein the diaphragm and materials that contact the medical gas are of a material without chemical, catalytic or absorptive interaction.

19. A method according to claim 17, wherein the pressure regulator is set to a pressure that maintains a flow rate of the gas through the flow orifice at a desired therapeutic level and wherein the flow orifice provides a critical flow of nitric oxide gas when the gas reaches sonic condition.

20. A non-electrical gas delivery system, comprising:
    a vessel containing a gas and a mechanically controlled pressure regulator to deliver a gas at a fixed flow rate to a mixing chamber;
    a face mask adapted to be sealed over a mouth and a nose, that allows the lungs to create a suction force on an inhalation tube to pull the gas and an external air towards the lungs; and
    a mechanically-variable flow restrictor and a flow indicator connecting the external air to a mixing chamber, where the external air is adjustable as a diluent in a gas dosage with adjustment to control the diluent gas mass flow.

* * * * *